US00PP22989P2

(12) United States Plant Patent
Zill

(10) Patent No.: US PP22,989 P2
(45) Date of Patent: Aug. 28, 2012

(54) MANGO TREE NAMED 'C-20'

(50) Latin Name: *Mangifera indica*
Varietal Denomination: C-20

(76) Inventor: Gary Edward Zill, Boynton Beach, FL (US)

( * ) Notice: Subject to any disclaimer, the term of this patent is extended or adjusted under 35 U.S.C. 154(b) by 31 days.

(21) Appl. No.: 12/932,074

(22) Filed: Feb. 17, 2011

(51) Int. Cl.
*A01H 5/00* (2006.01)

(52) U.S. Cl. ..... Plt./159

(58) Field of Classification Search ..... Plt./159
See application file for complete search history.

*Primary Examiner* — Susan McCormick Ewoldt
(74) *Attorney, Agent, or Firm* — Jondle & Associates, P.C.

(57) ABSTRACT

A new and distinct variety of mango tree (*Mangifera indica*), 'C-20' which is distinguished by the production of heavy and consistent crops of fruit which are 454 g average weight, oblong with a bluntly pointed apex and a large lateral beak. 'C-20' has a low and spreading growth habit with excellent disease tolerance and a small and manageable mature height of 457.2 cm. The skin color is bright yellow with a pink or crimson blush; thin, tender and adhesive skin, and a maturity date for harvesting and shipment of approximately mid June through July in South Florida. The flavor is excellent, rich and aromatic, with a strong component of coconut cream, a creamy smooth texture with no fiber or stringiness, a brix of 21% and a long flavor-life in storage.

1 Drawing Sheet

Genus and species: *Mangifera indica.*
Variety denomination: 'C-20'.

BACKGROUND OF THE NEW PLANT

The present invention comprises a new and distinct variety of mango, botanically known as *Mangifera indica*, and hereinafter referred to by the variety name 'C-20'. 'C-20' was developed through a cross conducted in Boynton Beach, Fla. in 2000 between the female parent 'Edward' (unpatented) and the male parent 'Gary' (unpatented). 'C-20' was selected as a single plant in July of 2006 and was first propagated in August of 2008 via grafting in Boynton Beach, Fla. The objective of the breeding program was to develop a mango tree with superior tree size (small), disease tolerance, productivity and fruit quality.

'C-20' has been propagated for approximately three years via grafting and has been found to retain its distinctive characteristics through successive asexual propagations via grafting from the mother tree.

Plant Breeder's Rights for this variety have not been applied for. 'C-20' has not been made publicly available or sold more than one year prior to the filing date of this application.

SUMMARY OF THE INVENTION

The following are the most outstanding and distinguishing characteristics of this new cultivar when grown under normal horticultural practices in Boynton Beach, Fla.

1. Small tree size;
2. Good and consistent productivity in South Florida;
3. Good disease tolerance;
4. Oblong to oval shaped fruit with lemon-yellow skin that turns a pink to crimson blush when exposed to direct sunlight and low nitrogen and lemon yellow to orange flesh; and 5. Soft and melting flesh with exceptional flavor of coconut cream and no fiber.

DESCRIPTION OF THE PHOTOGRAPHS

This new mango tree is illustrated by the accompanying photographs which show the bloom and the mature fruit of the tree in full color; the colors shown are as true as can be reasonably obtained by conventional photographic procedures. The photographs are of 4-year-old plants grown in Boynton Beach, Fla. in July, 2006.

DESCRIPTION OF THE NEW VARIETY

Figure 1:
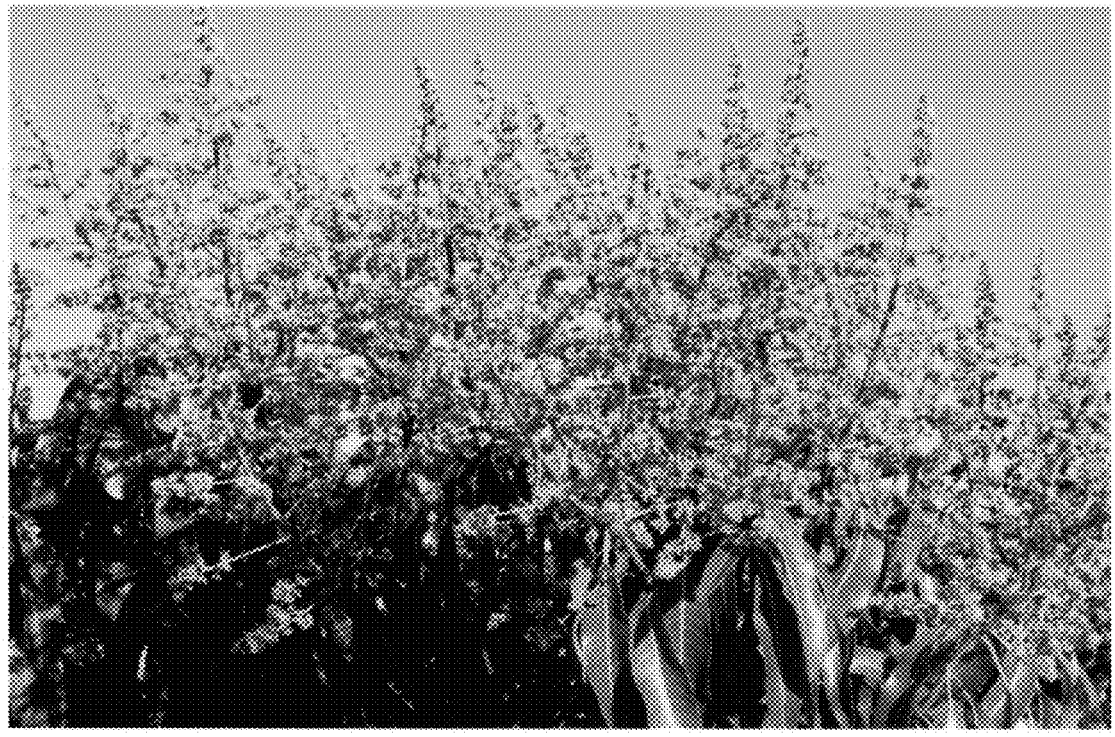
FIG. 1 shows the fully open bloom of a 4-year-old tree.
Figure 2:
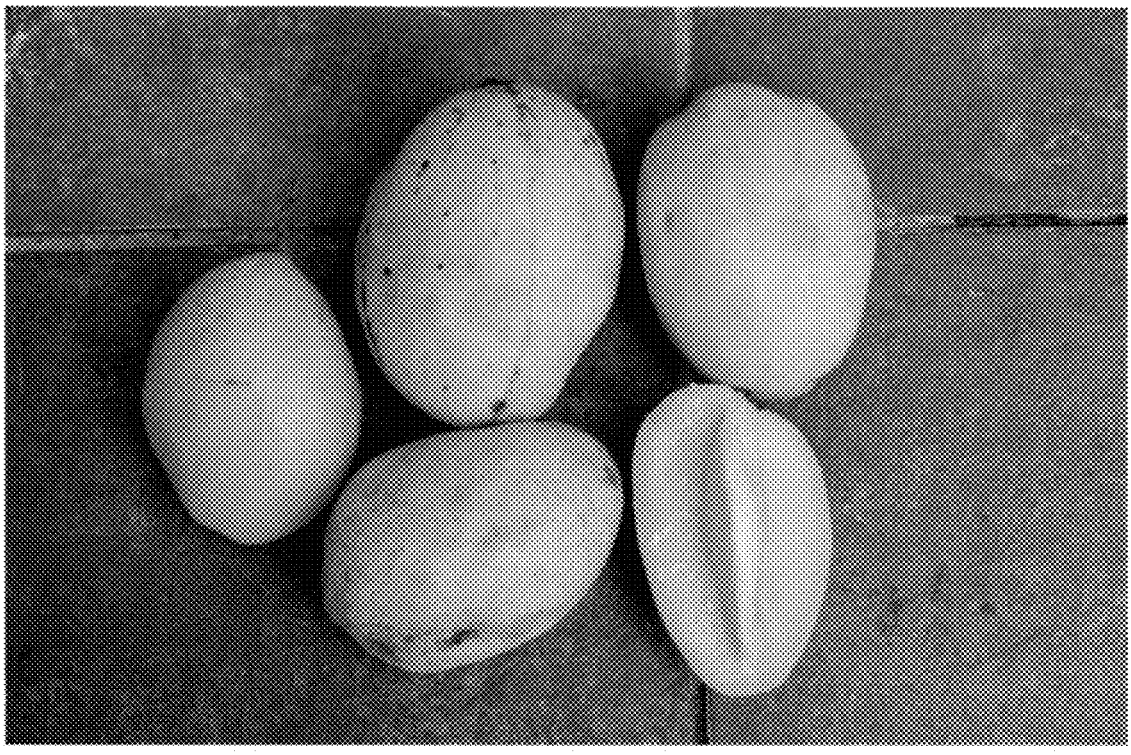
FIG. 2 shows the exterior and interior of the mature fruit.

The following detailed descriptions set forth the distinctive characteristics of 'C-20'. The data which define these characteristics were collected from asexual reproductions carried out in Boynton Beach, Fla. The plant history was taken on four- and five-year-old trees grown outdoors in Boynton Beach, Fla. in July, 2006 through 2009. Color readings were taken under natural light. Color references are primarily to The R.H.S. Colour Chart of The Royal Horticultural Society of London (R.H.S.) (2001 edition).

DETAILED BOTANICAL DESCRIPTION OF THE NEW PLANT

Classification:
*Family*.—Anacardiaceae.
*Botanical name*.—*Mangifera indica.*
*Denomination*.—'C-20'.

Tree:
*Growth habit*.—Low, spreading and open.
*Height*.—Less than 457.2 cm.
*Vigor*.—Medium to low.
*Regularity of bearing*.—Regular bearing except under extreme cold or warm winter conditions.

Trunk:
*Diameter.*—25.4 cm at 6 cm height.
*Surface texture.*—Smooth and regular.
*Color.*—Gray to tan, RHS 198A to RHS 158B.

Branches:
*Habit.*—Spreading and open.
*Size.*—Variable, due to the tree being pruned annually.
*Surface texture.*—Smooth.
*Color (one year old and older).*—Gray to tan, RHS 198A to RHS 158B.
*Color (immature, less than one year).*—Agathia to Imperial Jade, RHS 142A to RHS124A.

Leaves:
*Length.*—18.0 cm.
*Width.*—8.5 cm.
*Shape.*—Lanceolate.
*Apex.*—Acute with some twisting.
*Base.*—Broad angular.
*Margin.*—Smooth to slightly wavy.
*Shape in cross-section.*—Incurved.
*Pubescence.*—Absent.
*Color.*—Upper surface: Agathia to pea green, RHS 142A to RHS 149B. Lower surface: Agathia to pea green with a slight more yellow tint, RHS 142A to RHS 149B.
*Petiole.*—Length: 4.0 cm to 5.0 cm. Diameter: 0.3 cm to 0.5 cm. Color (mature): Willow grey, RHS 196A. Color (immature): Burgundy to wine, RHS 57A to RHS 58D.

Flower bud:
*Length.*—2.4 mm.
*Surface texture.*—Firm and waxy.
*Color.*—Chinese yellow to salmon, RHS 20B to RHS 27A.

Inflorescence:
*General.*—Flowers produced on multiple terminal inflorescence with thousands of individual flowers that typically set less than 1% in natural pollination.
*Date of bloom.*—Mid December to early March.

Flowers:
*Width.*—2.4 mm.
*Width when fully open.*—4.8 mm.
*Petals.*—Quantity per flower: 5. Color: White to cream to red with maturity, RHS 155A to RHS 159B to RHS 171B.
*Sepals.*—Quantity per flower: 5.
*Peduncle.*—Pink, red or green, RHS 62A, RHS 64A or RHS 140B.
*Penduncle length.*—2 mm or less.

Reproductive organs:
*Anther quantity.*—5 per flower.
*Anther color.*—White, RHS 155A.
*Ovary quantity.*—1.
*Stigma color.*—White and red, RHS 155A to RHS 159B.

Fruit:
*General.*—Ripe for commercial harvesting and shipment in approximately mid-June through July in South Florida. Typically, the fruit is on the tree for five to six months.
*Diameter.*—Ranges from 8.5 cm to 9.5 cm.
*Length.*—Ranges from 10.0 cm to 15.0 cm.
*Individual fruit weight.*—Ranges from of 330 g to 600 g (average is 454 g).
*Shape.*—Oblong to oval with an undulating skin surface, a rounded base, slender stem with a squared insertion, no cavity, and a bluntly pointed apex with a large lateral beak.
*Pedicel.*—Shape: Conical. Diameter: 0.4 cm.
*Stem cavity.*—Little or no stem cavity depression.
*Stem.*—Color: Brown to gray, RHS 190C to RHS 198C. Length: 10.0 cm to 15.0 cm. Diameter: 0.4 cm.
*Seed.*—Shape: Oblong. Length: 9.5 cm. Breadth: 4.3 cm. Thickness: 2.0 cm. Weight: 31.6 g. Color: RHS 159C.
*Skin.*—Thickness: Thin, tender and adhesive. Smoothness: Moderately undulating. Lenticels: Numerous, large, russet lenticels. Color: Lemon to deep yellow with an orange to pink blush, RHS 12A to RHS 13A with RHS 21A to RHS 29B if exposed to the sun; more blush color when fruit are grown under low nitrogen conditions and with increased sun exposure and cool temperatures during development.
*Flesh.*—Texture: Soft, melting and juicy with no fiber. Color: Lemon yellow to orange, RHS 12A to RHS 21B. Fiber: Absent. Flavor: Flavor is like coconut cream; rich, aromatic and sweet with a brix content of 21%. Fragrance: Slight and pleasant. Texture: Firm. Softening: Time to softening (ripening) depends on stage of maturity (3 to 10 days); softening is rapid and uniform once it begins; flesh firmness maintained for several days at room temperature. Use: Fresh fruit, fresh cut or for pulp. Keeping quality: Above average shipping and shelf life.

Disease and insect resistance: Good tolerance to anthracnose (*Colletotricum gloeosporioides*). Moderate susceptibility to powdery mildew (*Oidium mangiferae*).

Physiological conditions: Sap burn is not a problem in Florida, but in areas with severe incidence it is thought that there may be problems given the skin color.

COMPARISON WITH PARENTAL AND COMMERCIAL VARIETIES

'C-20' differs from the female parent 'Edward' (unpatented) in that 'C-20' fruits in July, is shorter in height and has oblong shaped fruits, while 'Edward' fruits in May to June, is taller in height and has oblate shaped fruit.

'C-20' differs from the male parent 'Gary' (unpatented) in that 'C-20' has oblong shaped fruit with coconut cream flavored flesh and has large leaves, while 'Gary' has oval shaped, small fruit and a small leaf size.

'C-20' differs from the commercial variety 'Ataulfo' (unpatented) in that 'C-20' has oblong shaped fruit, is shorter in height and has a fruit skin with a pink blush, while 'Ataulfo' has long and slender shaped fruit, is taller in height and has fruit skin with no blush.

I claim:

1. A new and distinct variety of mango tree named 'C-20' as described and shown herein.

* * * * *